US00PP33696P2

(12) United States Plant Patent
van Sambeek

(10) Patent No.: US PP33,696 P2
(45) Date of Patent: Nov. 23, 2021

(54) ***PENSTEMON* PLANT NAMED 'DOPENPEPREDIM'**

(50) Latin Name: *Penstemon hartwegii*
Varietal Denomination: Dopenpepredim

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/203,250

(22) Filed: Mar. 16, 2021

(51) Int. Cl.
*A01H 5/02* (2018.01)
*A01H 6/68* (2018.01)

(52) U.S. Cl.
USPC ..... Plt./465

(58) Field of Classification Search
USPC ..... Plt./465, 263.1
CPC ... A01H 5/02; A01H 5/00; A01H 6/68; A01H 6/00; A01H 1/107
See application file for complete search history.

*Primary Examiner* — June Hwu
(74) *Attorney, Agent, or Firm* — C. Anne Whealy

(57) ABSTRACT

A new and distinct cultivar of *Penstemon* plant named 'Dopenpepredim', characterized by its upright plant habit; vigorous growth habit and rapid growth rate; freely branching habit; freely flowering habit; long flowering period; relatively large red-colored flowers with white-colored centers; and good garden performance.

1 Drawing Sheet

Botanical designation: *Penstemon hartwegii.*
Cultivar denomination: 'DOPENPEPREDIM'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Jan. 13, 2021, application number 2021/0125. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Penstemon* plant, botanically known as *Penstemon hartwegii* and hereinafter referred to by the name 'Dopenpepredim'.

The new *Penstemon* plant is a product of a planned breeding program conducted by the Inventor in Aalsmeer, The Netherlands. The objective of the breeding program was to create new freely-branching *Penstemon* plants with attractive flower color.

The new *Penstemon* plant originated from a self-pollination in July, 2014 in Aalsmeer, The Netherlands, of a proprietary selection of *Penstemon hartwegii* identified as code number PE13-000001-007, not patented. The new *Penstemon* plant was discovered and selected by the Inventor as a single flowering plant from within the progeny of the stated self-pollination in a controlled environment in Aalsmeer, The Netherlands in May, 2015.

Asexual reproduction of the new *Penstemon* plant by terminal vegetative cuttings in a controlled environment in Aalsmeer, The Netherlands since June, 2015 has shown that the unique features of this new *Penstemon* plant are stable and reproduced true to type in successive generations.

SUMMARY OF THE INVENTION

Plants of the new *Penstemon* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopenpepredim'. These characteristics in combination distinguish 'Dopenpepredim' as a new and distinct *Penstemon* plant:

1. Upright plant habit.
2. Vigorous growth habit and rapid growth rate.
3. Freely branching habit.
4. Freely flowering habit.
5. Long flowering period.
6. Relatively large red-colored flowers with white-colored centers.
7. Good garden performance.

Plants of the new *Penstemon* differ primarily from plants of the parent selection in flower color as plants of the new *Penstemon* have red-colored flowers with white-colored throats whereas plants of the parent selection have solid red-colored flowers.

Plants of the new *Penstemon* can also be compared to plants of *Penstemon hartwegii* 'PepTalk Red', not patented. In side-by-side comparisons, plants of the new *Penstemon* and 'PepTalk Red' differ in the following characteristics:

1. Plants of the new *Penstemon* are shorter than plants of 'PepTalk Red'.
2. Flowers of plants of the new *Penstemon* open more broadly with development than flowers of plants of 'PepTalk Red'.

BRIEF DESCRIPTION OF THE PHOTOGRAPH

The accompanying colored photograph illustrates the overall appearance of the new *Penstemon* plant showing the colors as true as it is reasonably possible to obtain in colored reproductions of this type. Colors in the photograph may differ slightly from the color values cited in the detailed botanical description which accurately describe the colors of the new *Penstemon* plant. The photograph is a top perspective view of typical flowering plant of 'Dopenpepredim' grown in a container.

DETAILED BOTANICAL DESCRIPTION

The aforementioned photograph and following observations, measurements and values describe plants grown during the summer in 17-cm containers initially in a glass-covered greenhouse and finished in an outdoor nursery in Aalsmeer, The Netherlands and under cultural practices typical of commercial *Penstemon* production. During the production of the plants, day temperatures averaged 21° C. and night temperatures averaged 15° C. Plants were 27 weeks old when the photograph and detailed description were taken. In the following description, color references are made to The Royal Horticultural Society Colour Chart, Second Edition, except where general terms of ordinary dictionary significance are used.

Botanical classification: *Penstemon hartwegii* 'Dopenpepredim'.

Parentage:

*Female, or seed, parent*.—Proprietary selection of *Penstemon hartwegii* identified as code number PE13-000001-007, not patented.

*Male, or pollen, parent*.—Proprietary selection of *Penstemon hartwegii* identified as code number PE13-000001-007, not patented.

Propagation:

*Type*.—By vegetative cuttings.

*Time to initiate roots, summer*.—About 12 days at temperatures about 26° C.

*Time to initiate roots, winter*.—About 16 days at temperatures about 23° C.

*Time to produce a rooted young plant, summer*.—About 16 days at temperatures about 23° C.

*Time to produce a rooted young plant, winter*.—About 20 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright plant habit; vigorous growth habit and rapid growth rate.

*Plant height*.—About 60 cm.

*Plant width* (*spread*).—About 50 cm.

*Lateral branches*.—Quantity of lateral branches: Freely branching habit, about twelve lateral branches develop per plant. Length: About 50 cm. Diameter: About 1.2 cm. Internode length: About 3.5 cm. Strength: Strong. Aspect: Upright to about 30° from vertical. Texture and luster: Smooth, glabrous; glossy. Color, developing and developed: Close to 144B.

Leaf description:

*Arrangement*.—Opposite, simple; decussate and sessile.

*Length*.—About 10.5 cm.

*Width*.—About 3.2 cm.

*Shape*.—Lanceolate.

*Apex*.—Acuminate.

*Base*.—Cuneate.

*Margin*.—Entire to irregularly dentate.

*Texture and luster, upper surface*.—Smooth, glabrous; glossy.

*Texture and luster, lower surface*.—Smooth, glabrous; matte.

*Venation pattern*.—Pinnate.

*Color*.—Developing leaves, upper surface: Close to 139A. Developing leaves, lower surface: Close to 137B. Fully expanded leaves, upper surface: Close to 137A; venation, close to 143A. Fully expanded leaves, lower surface: Close to 137C; venation, close to 145B.

Flower description:

*Flower shape, arrangement and flowering habit*.—Single bi-labiate flowers arranged on terminal racemes; flowers face mostly outwardly; freely flowering with about 52 flowers developing per inflorescence; about 664 flowers developing per plant during the flowering season.

*Fragrance*.—Faintly fragrant; pleasant.

*Time to flower*.—Early flowering habit, plants begin to flower about 18 weeks after planting.

*Natural flowering season*.—Long flowering period, plants flower about eight to ten weeks during June and July in The Netherlands; flowers not persistent.

*Flower buds*.—Length: About 2 cm. Diameter: About 8 mm. Shape: Elongate ovoid. Texture and luster: Slightly pubescent; semi-glossy. Color: Close to 46A.

*Inflorescence height*.—About 21 cm.

*Inflorescence diameter*.—About 11 cm.

*Flower width* (*horizontal*).—About 3 cm.

*Flower length* (*vertical*).—About 3 cm.

*Flower depth*.—About 3.5 cm.

*Flower throat diameter*.—About 1.5 cm.

*Flower tube length*.—About 2.5 cm.

*Flower tube diameter*.—About 1.5 cm.

*Petals*.—Arrangement: Five, fused into a tube; bilabiate, upper lip with two upper petals and lower lip with three lower petals. Lobe length, upper and lower lips: About 1 cm. Lobe width, upper and lower lips: About 1.5 cm. Lobe shape: Obovate. Lobe apex: Acute. Lobe margin: Entire; slightly undulate. Lobe texture and luster, upper surface: Smooth, glabrous; semi-glossy. Lobe texture and luster, lower surface: Pubescent; semi-glossy. Throat, texture and luster: Mostly smooth to slightly pubescent; semi-glossy. Tube, texture and luster: Pubescent; semi-glossy. Color: Lobes, when opening, upper and lower surfaces: Close to 45A. Lobes, fully opened, upper and lower surfaces: Close to 45B; venation, close to 45B; color becoming close to 45D with development. Flower throat: Close to 155D; venation, close to 155D; color does not change with development. Flower tube: Close to 45B; venation, close to 45B; color becoming close to 45D with development.

*Sepals*.—Arrangement: Five sepals fused in a single whorl. Length: About 8 mm. Width: About 4 mm. Shape: Rhomboid. Apex: Acute. Margin: Entire. Texture and luster, upper surface: Pubescent; semi-glossy. Texture and luster, lower surface: Smooth, glabrous; semi-glossy. Color: When opening and fully developed, upper surface: Close to 141A and 79A. When opening and fully developed, lower surface: Close to 141A.

*Peduncles*.—Length: About 7 cm. Diameter: About 2 mm. Aspect: Upright to about 5° from vertical. Strength: Moderately strong. Texture and luster: Pubescent; glossy. Color: Close to 144B.

*Pedicels*.—Length: About 5 mm. Diameter: About 1 mm. Aspect: Upright to about 10° from vertical. Strength: Weak. Texture and luster: Pubescent; glossy. Color: Close to 144B and/or close to 83A.

*Reproductive organs*.—Stamens: Quantity per flower: Four. Filament length: About 2 cm. Filament color: Close to 155D. Anther size: About 3 mm by 3 mm. Anther shape: Rounded. Anther color: Close to 86A. Pollen amount: Abundant. Pollen color: Close to 155A. Pistils: Quantity per flower: One. Pistil length: About 2 cm. Style length: About 1.9 cm. Style color: Close to 74A and 75C. Stigma diameter: About 0.5 mm. Stigma shape: Capitate. Stigma color: Close to 155A. Ovary color: Close to 143A.

*Seeds and fruits*.—To date, seed and fruit development have not been observed on plants of the new *Penstemon*.

Garden performance: Plants of the new *Penstemon* have been observed to have good garden performance and tolerate rain, wind and temperatures ranging from −15° C. to 35° C. and to be suitable for USDA Hardiness Zone 7.

Pathogen & pest resistance: To date, plants of the new *Penstemon* have not been observed to be resistant to pathogens and pests common to *Penstemon* plants.

It is claimed:

1. A new and distinct *Penstemon* plant named 'Dopenpepredim' as illustrated and described.

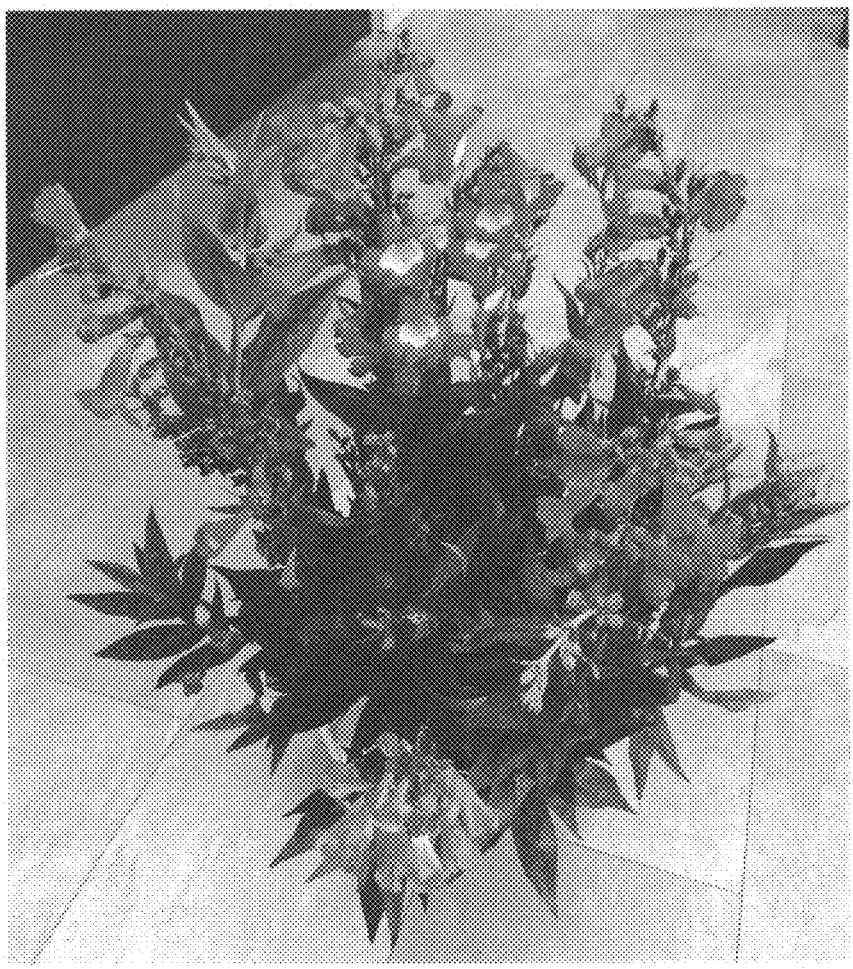

* * * * *